United States Patent [19]

Stephenson et al.

[11] Patent Number: 5,246,656

[45] Date of Patent: Sep. 21, 1993

[54] METHOD FOR FORMING AIR FLOW CONTROL ORIFICE IN AN INFLATED BLANKET

[75] Inventors: James G. Stephenson; Eugene L. Kilbourn, both of Marshall; Peter C. Kempf, Dexter, all of Mich.

[73] Assignee: Progressive Dynamics, Inc., Marshall, Mich.

[21] Appl. No.: 915,254

[22] Filed: Jul. 20, 1992

[51] Int. Cl.⁵ .................................................. B26F 1/20
[52] U.S. Cl. ..................................... 264/153; 264/154; 264/156; 83/30; 83/660
[58] Field of Search ............... 264/153, 154, 155, 156; 425/289, 290, 291; 83/30, 658, 659, 660, 669, 681

[56] References Cited

U.S. PATENT DOCUMENTS

| | | | |
|---|---|---|---|
| 2,142,728 | 1/1939 | Kienzle | 83/660 |
| 2,748,863 | 5/1956 | Benton | 264/156 |
| 3,546,327 | 12/1970 | Ruda | 264/156 |
| 3,562,368 | 2/1971 | Bridgeford | 264/156 |
| 3,599,445 | 2/1971 | Hougen | 83/660 |
| 3,682,028 | 8/1972 | Clayton et al. | 83/660 |
| 3,956,956 | 5/1976 | Bertlolf | 83/660 |
| 4,176,567 | 12/1979 | Weisberg | 83/660 |
| 4,653,363 | 3/1987 | Lang | 83/30 |
| 5,125,238 | 6/1992 | Ragan et al. | 62/259.3 |

*Primary Examiner*—Jay H. Woo
*Assistant Examiner*—Duane S. Smith
*Attorney, Agent, or Firm*—Beaman & Beaman

[57] ABSTRACT

The invention pertains to the method for forming air flow control orifices in a patient body temperature regulating blanket consisting of an inflated envelope defined by thin plastic film wherein temperature controlled air flows through the blanket orifices upon the patient's body. The blanket side disposed toward the patient is pierced by a sharp pointed punch having a plurality of intersecting facets defining sharpened intersecting edges. The punch apex and facet intersecting edges are related to the moving film in such a manner that the penetration of the punch forms a plurality of flexible valve flaps, and the valve flaps engaging the patient's body will be retained in a closed condition to restrain air flow through those orifices engaging the body to prevent exposure to excessive air temperatures.

6 Claims, 1 Drawing Sheet

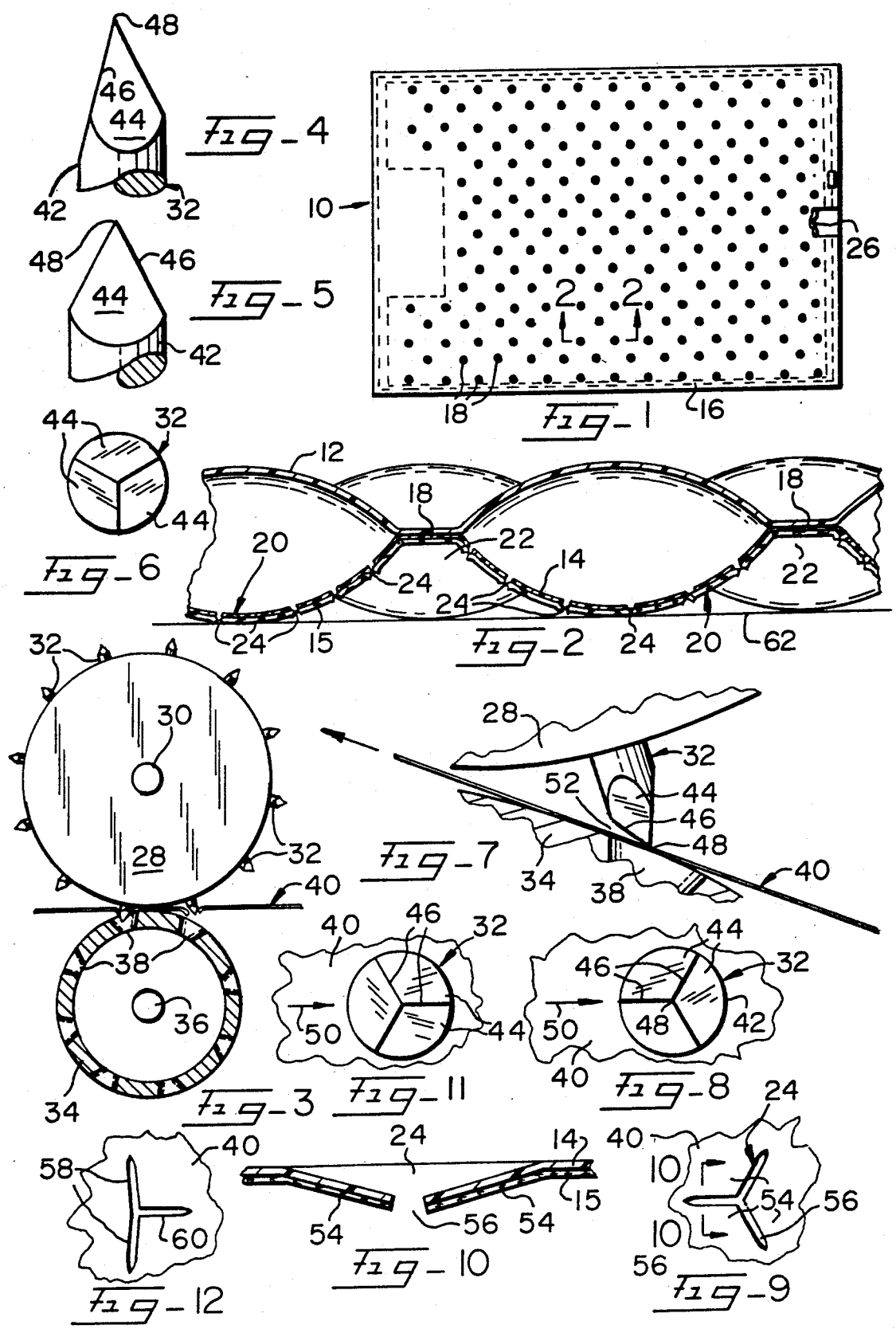

METHOD FOR FORMING AIR FLOW CONTROL ORIFICE IN AN INFLATED BLANKET

BACKGROUND OF THE INVENTION

1. Field of the Invention

The invention pertains to the forming of air flow control orifices in a film or web by the use of a multiple faceted sharp punch wherein the punch forms a plurality of flexible valve flaps which define the orifice.

2. Description of the Related Art

Post-surgery medical patients often experience body temperature fluctuations, and a treatment for such conditions includes covering the patient's body with a thermal blanket. The thermal blanket may be inflated with a warm pressurized air, and orifices formed in the blanket side disposed toward the patient permit the warm air to be discharged from the blanket envelope upon the patient. Such a single use patient warming blanket is shown in the assignee's U.S. Pat. No. 5,125,238.

As will be appreciated from the above identified patent, the lower side of the blanket disposed toward the patient is provided with a plurality of orifices through which the warm air flows toward the patient. Preferably, the blanket lower side outer surface is provided with a non-woven, fibrous layer which, though thin, is sufficient to increase the frictional characteristics of the blanket envelope forming material, which is usually a thin plastic film of a flexible nature.

Usually, the warming blanket is directly placed upon the patient's body wherein the lower blanket surface, i.e. the non-woven material, will directly engage the patient's body. As disclosed in the assignee's above identified patent, the blanket is formed of a plurality of cells by heat sealing the blanket envelope upper and lower films at spaced locations resulting in a blanket form having a plurality of projections or protrusions intermediate recesses or depressions located adjacent the film welded or staked points.

The air control orifices formed in the blanket lower film and non-woven material are usually evenly spaced over the lower surface of the blanket, and some of the orifices will be defined at the lowermost regions of the bulbous projections which directly engage the patient's body. Accordingly, air flowing from such orifices in direct engagement with the patient's body will tend to impose a higher temperature air upon the patient's body than the air discharged from the orifices formed in the blanket recesses which are spaced from the patient's body permitting the air to be diffused, cooled and distributed prior to engaging the patient's body.

Heretofore, the orifices of a patient warming blanket have not been capable of automatically sensing the presence of the patient's body and preventing direct exposure of the air released from the blanket.

SUMMARY OF THE INVENTION

Objects of the Invention

It is an object of the invention to provide a method of forming an air flow control orifice in an inflated blanket wherein air flow from orifices directly in contact with the patient's body will be restricted.

Another object of the invention is to provide a method for forming an air flow control orifice in an inflated blanket wherein the orifices are defined by a plurality of flexible valve flaps capable of automatically closing under the influence of external pressures to restrict air flow from the orifice.

Yet another object of the invention is to provide a method of controlling the flow of air from an inflated blanket wherein air flow is through a plurality of orifices, each of the orifices including a plurality of flexible valve flaps capable of automatically closing when directly engaging the patient's body to restrict air flow from such orifices.

An additional object of the invention is to provide a method for punching air flow control orifices in a thin film or web wherein the orifices are defined by a plurality of flexible valve flaps of substantially identical configuration.

In the practice of the invention, a patient warming, or cooling, blanket is formed by a pair of flexible thermoplastic sheets of film heat sealed at their periphery, and at spaced internal locations to define an envelope. A fitting communicating with the blanket envelope interior permits pressurized air to be supplied to the blanket for inflation purposes. The lower side of the blanket, i.e. the blanket side disposed toward the patient covered by the blanket, includes an outer non-woven fibrous material to provide a friction surface, and the lamination of the fibrous material and the lower film is provided with a plurality of air flow control orifices through which the air within the blanket is directed toward the patient and bed supporting the patient.

The air flow control orifices are punched into the blanket lower surface film and non-woven material by a sharp punch having an apex defined by a plurality of intersecting facets. Preferably, the facets are planar, three in number arranged at equal 120° spacings about the longitudinal axis of the punch, and intersecting each other to define sharp linear intersecting edges.

The punch facets and intersecting edges are related to the direction of travel of the film or web to be punched such that a linear edge is aligned with, i.e. parallel to, the direction of movement of the film as it passes between a roller carrying a plurality of punches, and a back-up or support roller which supports the film as it is being punched. By so relating the punch intersecting edge to the direction of film movement, an air control orifice is defined in the film and non-woven material which consists of three intersecting slits disposed at 120° to each other and the film and non-woven material intermediate the slits defines flexible identical valve flaps which, when maintained in a plane substantially equal to the normal plane of the associated blanket surface, substantially closes the associated orifice to air flow therethrough. Such a relationship occurs when the orifice is directly engaging the patient's body such that the patient's body engages the valve flaps and maintains the valve flaps within the plane of the orifice.

Accordingly, by forming the air flow control orifices in an inflatable blanket in accord with the invention, direct exposure of the patient's body to warm air due to the orifice touching the patient's body is minimized, and the orifices of the invention permit a patient warming blanket to be economically formed which is capable of automatically controlling the air flow upon the patient.

BRIEF DESCRIPTION OF THE DRAWING

The aforementioned objects and advantages of the invention will be appreciated from the following description and accompanying drawings wherein:

FIG. 1 is a top plan view of a patient warming blanket of the type in which the air flow control orifices of the invention may be defined, FIG. 2 is an enlarged detail elevational sectional view as taken along Section 2—2 of FIG. 1, FIG. 3 is a side elevational, partially schematic, view of the roller apparatus for forming the air control orifices in accord with the invention, FIG. 4 is a detail view of the punch penetrating end illustrating an intersecting edge, FIG. 5 is a detail view of the punch intersecting end illustrating a full facet face, FIG. 6 is an end view of the punch penetrating end, FIG. 7 is an enlarged detail view illustrating the relationship of the punch to the film upon engagement of the punch apex with the film, and prior to penetration, FIG. 8 is a schematic view illustrating the end of the orifice forming punch and the relationship of the punch intersecting edges to the direction of film movement during orifice forming, FIG. 9 is a detail view of an air control orifice formed in accord with the invention by a punch oriented as shown in FIG. 8, FIG. 10 is an enlarged elevational sectional view of an air control orifice formed in accord with the invention as taken along Section 10—10 of FIG. 9, FIG. 11 is a view similar to FIG. 8 illustrating a non-preferred orientation of the punch facets to the direction of film movement during penetration, and FIG. 12 is an enlarged detail illustration of an air flow control orifice if formed by the punch orientation of FIG. 11.

DESCRIPTION OF THE PREFERRED EMBODIMENT

A patient warming blanket utilizing the concepts of the invention is shown in FIG. 1, and may be identical to the assignee's blanket as disclosed in U.S. Pat. No. 5,125,238, the disclosure of this patent being incorporated herein. It is to be appreciated that the blanket 10, while usually employed to flow warm air over a patient for body temperature control purposes, may also be used for patient cooling as it is within the concepts of the invention to inflate the blanket 10 with cool air in the event that body cooling is required, and the air flow control orifices of the invention operate identically regardless of the air temperature.

Basically, the blanket 10 consists of an upper synthetic thermoplastic flexible film 12 and a lower film 14 which define an air containable envelope. Preferably, the outer surface of the film 14 has a non-woven material 15 laminated thereto to increase the frictional characteristics of the outer surface of the lower portion of the blanket. The peripheral edge 16 of the blanket 10 is heat sealed to define a closed envelope, and intermediate its periphery the films 12 and 14 are welded or staked together by heat sealing to define a plurality of interconnected cells which form outwardly extending bulbous convex projections 20, FIG. 2, having recesses 22 defined therebetween adjacent the stakes 18.

The lower side of the blanket defined by film 14 and laminated material 15 is provided with a plurality of air flow control orifices 24 substantially evenly spaced over the area of the lower surface of the blanket 10. Heated, or cooled, air is supplied to the interior of the blanket 10 through the inlet fitting 26, and air flows from the orifices 24 upon the patient as later described.

The air flow control orifices 24 are formed by apparatus shown in FIG. 3 consisting of a punch roller 28 rotating about shaft 30. A plurality of radially extending punches 32 extend from the roller 28, and the width of the roller 28 will be substantially equal to the width of the blanket, i.e. the vertical height of the blanket 10 as illustrated in FIG. 1.

A back-up roller 34 rotates about a shaft 36 which is parallel to shaft 30, and the back-up roller 34 includes a plurality of holes 38 for receiving the punches 32 as the rollers 28 and 34 rotate in synchronization so that the punches 32 are properly received within the holes 38.

The film 40, FIG. 3, which is used to define the lower side of the blanket 10 and consists of the lamination of the film 14 and non-woven material 15, passes between the rollers 28 and 34, and is penetrated by the punches 32 as it passes between the rollers.

The configuration of the punches 32 will be appreciated from FIGS. 4-6 wherein the punches 32 are of a cylindrical configuration having an outer cylindrical surface 42. At the outer ends of the punch, the punch includes a plurality of facets 44 which are preferably planar in configuration and intersect at intersecting edges 46 to define a sharp apex 48.

In the preferred embodiment, three facets 44 are employed which are of identical configuration such that the intersecting edges 46 will be disposed at 120° to each other with respect to the longitudinal axis of the associated punch 32, and the intersecting edges 46 are of a linear configuration defining a sharp cutting edge.

The punches 32 are oriented within the punch roller 28 such that an intersecting facet edge is parallel to the direction of film movement as indicated by the arrow 50, FIG. 8. Also, the diameter of the punch roller 28 and the back-up roller 34, and the length of the punch 32, and the configuration of the facets 44 is such that the initial engagement between the punch 32 and the film 40 is at the punch apex 48 as illustrated in FIG. 7. The angle of the film 40 to the punch is such that the intersecting edge 46 closest to the film 40 will be spaced from the film 40 to define a clearance 52, FIG. 7, at the time that the apex 48 is engaging the film 40. The film 40 will be translated at a velocity equal to the rate of movement of the punches 32 and in a direction parallel to the direction of movement of the punches.

Accordingly, the apex 48 will initially penetrate the film 40 followed by the leading intersecting edge 46 which will cut a slit in the film. Thereafter, as the punch 32 is received within the aligned hole 38 of the back-up roller 34 the "trailing" intersecting edges 46 will penetrate the film or web 40 and also cut slits in the film.

With reference to FIG. 9, the desired air flow control orifice 24 is shown. The orifice 24 consists of a plurality of flexible valve flaps 54 formed of the material of the film 40 as defined by the slits 56 which are the slits cut in the film by the punch intersecting edges 46. In FIG. 9 the width of the slits 56 is exaggerated for purpose of illustration.

As will be appreciated from FIG. 9, by aligning the punch intersecting edges 46 to the direction of film movement 50 as shown in FIG. 8, the valve flaps 54 will be of identical configuration each defining a 120° included angle. A side view of the air flow control orifice 24 as shown in FIG. 9 appears in FIG. 10 wherein the valve flaps 54 are slightly downwardly deflected. The resilient nature of the film 40 tends to normally maintain the valve flaps 54 substantially parallel to the unpunctured adjacent portion of the film 40 as defined by the film layer 14 and the non-woven material 15, and the presence of the pressurized air within the blanket 10 will cause the valve flaps 54 to outwardly deflect as shown in FIG. 10 permitting air to pass through the slits 56.

By forming the air flow control orifices 24 in the aforedescribed manner, those orifices 24 which are directly engaging the patient's body as represented at 62 in FIG. 2, will be maintained "closed", i.e. substantially parallel to the film 14 and material 15 substantially eliminating the flow of air through the orifice directly against the patient's body. This closing of the orifices 24 directly engaging the patient's body 62 will prevent "hot spots" upon the body with the attendant possible discomfort. However, those orifices 24 located within the recesses 22 above the body 62 will not be engaging the body and the valve flaps 54 thereof will outwardly deform as shown in FIG. 10 permitting the air within the blanket envelope to flow through the slits 56 warming the body, and yet the distance of those orifices 24 from the body through which air is flowing is sufficient to prevent localized temperature "hot spots" and the use of flow control orifices 24 in accord with the invention permits the blanket 10 to provide a more uniform and comfortable heating of the body than previous constructions.

If the punch 32 is oriented to the direction of movement of film 40 as indicated at 50 in FIG. 11 wherein the leading intersecting edges 46 which initially engage the film 40 are obliquely disposed to the direction of film travel the resulting valve flaps as defined by the intersecting edges will not be equal. FIG. 12 represents the orientation of the slots defined in the film 40 if the punch intersecting edges 46 are oriented as shown in FIG. 11. In such instance, the slits 58 defined by the leading intersecting edges 48 will be substantially in alignment, while the trailing intersecting edge 46 will define a slit 60. As clearly apparent from FIG. 12 identical film portions intermediate the slots 58 and 60 do not exist and the symmetry and uniformity of valve flap forming achieved with the arrangement illustrated in FIGS. 8 and 9 is not attained. Accordingly, the orientation of the punch intersecting edges shown in FIG. 8 is strongly preferred wherein the leading intersecting edge 46 is parallel to the direction of film movement during penetration of the film by the punch 32.

A patient body temperature control blanket 10 utilizing air flow control orifices 24 formed in the described manner overcomes many of the problems attendant with previous patient warming blankets and it is appreciated that various modifications to the inventive concepts may be apparent to those skilled in the art without departing from the spirit and scope of the invention.

We claim:

1. The method of forming an air flow control orifice in an inflated blanket to be placed upon a patient's body having a body engaging side defined by a thin flexible material comprising the step of:
   a) puncturing a plurality of spaced orifices in the body engaging side defined by a plurality of radially related slits to define orifices each formed by a normally closed an opening consisting of a plurality of flexible valve flaps having flexible ends said valve flaps pivoting to an open air flow position out of the opening upon the blanket being inflated if in non-engagement with the patient's body associated with the blanket and said valve flaps being retained in an airflow restrictive position within the opening if in engagement with the patient's body associated with the blanket.

2. The method of forming an air flow control orifice as in claim 1 wherein the orifice is defined by three valve flaps.

3. The method of puncturing a thin web of flexible material to define an air flow control orifice formed by a plurality of flexible valve flaps formed of the flexible material using a pointed punch having an apex defined by a plurality of elongated facets converging toward the apex and intersecting in sharp facet edges each having a length comprising the steps of:
   a) translating the web of flexible material in a given direction of movement at a given linear velocity.
   b) rotating the punch about an axis whereby the punch apex is translating through an arc at a velocity substantially equal tot he web linear velocity and in a direction parallel to said web given direction of movement,
   c) disposing an elongated punch fact edge in a direction parallel to and opposite to said web given direction of movement and toward the approaching web, and
   d) penetrating the web with the punch apex and facet edges whereby the punch facet edges define elongated slits in the web which define the flexible valve flaps, the configuration and spacing of the valve flaps corresponding to the spacing of the facet edges and a slit being parallel to said web given direction of movement.

4. In the method of puncturing a thin web as in claim 3, three facets being defined upon the punch.

5. In the method of puncturing a thin web as in claim 4, said facet edges being spaced 120° about the longitudinal axis of the punch.

6. In the method of puncturing a thin web as in claim 3 comprising the step of orienting and angularly relating the punch apex to the web prior to penetration of the web such that the punch apex engages the web prior to the web being engaged by a facet edge whereby the web is initially penetrated by the punch apex.

* * * * *